United States Patent
Phillips

Patent Number: 6,102,906
Date of Patent: Aug. 15, 2000

[54] SYSTEM AND METHOD FOR THE TREATMENT OF HYPEROPIA AND MYOPIA

[76] Inventor: Andrew F. Phillips, 622 W. Duarte, Suite 101, Arcadia, Calif. 91007

[21] Appl. No.: 09/157,191
[22] Filed: Sep. 18, 1998

Related U.S. Application Data

[60] Provisional application No. 60/059,705, Sep. 22, 1997.

[51] Int. Cl.$^7$ ..................................................... A61B 18/08
[52] U.S. Cl. .................................. 606/28; 606/29; 606/31
[58] Field of Search ........................ 606/27–31; 219/229, 219/236, 241

[56] References Cited

U.S. PATENT DOCUMENTS

| | | | |
|---|---|---|---|
| 4,481,948 | 11/1984 | Sole | 606/45 |
| 4,907,585 | 3/1990 | Schachar | 606/28 |
| 5,766,171 | 6/1998 | Silvestrini | 606/49 |
| 6,006,756 | 12/1999 | Shadduck | 128/899 |
| 6,024,095 | 2/2000 | Stanley, III | 606/27 |
| 6,036,688 | 2/2000 | Edwards | 606/34 |

*Primary Examiner*—Lee Cohen
*Attorney, Agent, or Firm*—David P. Gordan; David S. Jacobosn; Thomas A. Gallagher

[57] ABSTRACT

A system for reducing the radius of curvature of a cornea is provided which includes a device having an electrically-resistive ring, an insulative shaft coupled to the ring, and an electrical lead coupled to the ring, and an insulative handle coupled to the ring which facilitates manipulating the ring for placement on and removal from the cornea of the eye and through which the lead extends. The lead is couplable to a current source. According to a preferred aspect of the invention, a function generator is provided between the current source and the ring to generate a function of heat energy provided to the ring. The function generator permits very precise applications of current to the ring, and may be configured to heat the ring to a desired temperature, to maintain the temperature for a predetermined amount of the time, or to provide a heat profile. An astigmatism correction device, preferably operable in conjunction with the hyperopia heating device, is also provided. The device includes an element which is shaped to provide heat energy at two location 180° apart, and preferably fits within the annular opening of the hyperopia correction device. The device may be actively heated by the same power source as the hyperopia correction device, may be passively heated by the hyperopia correction device, or may be separately heated.

23 Claims, 4 Drawing Sheets

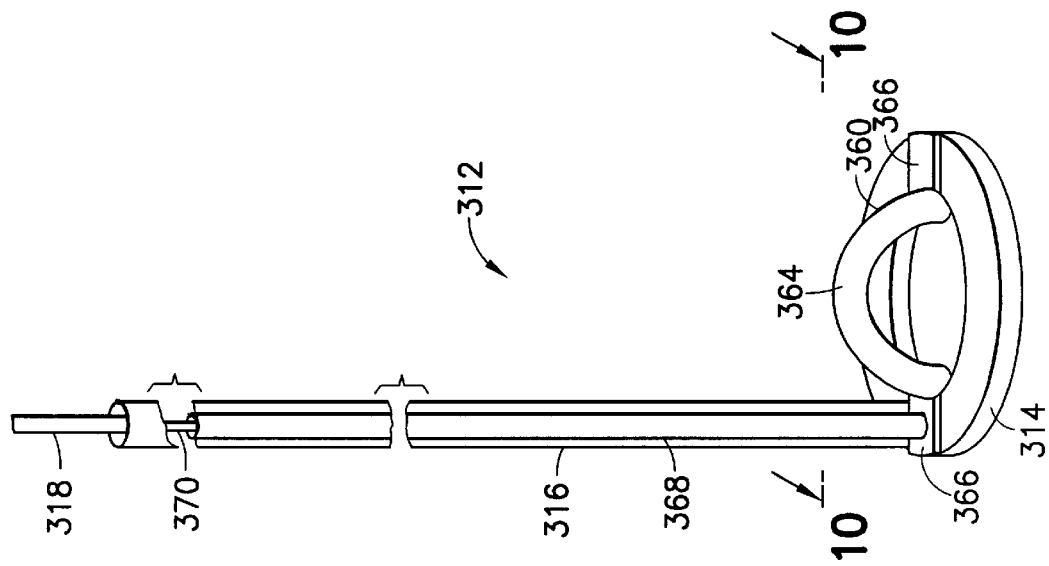
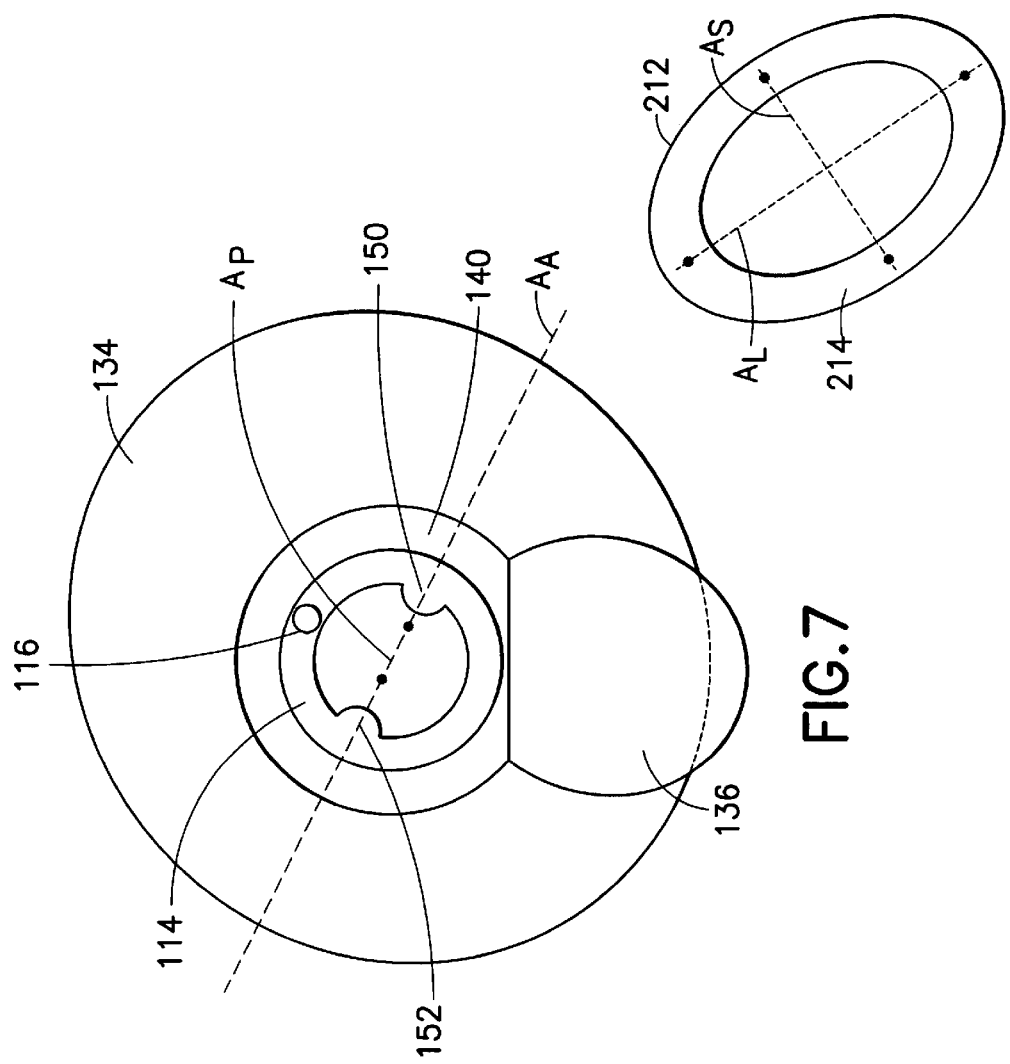

SYSTEM AND METHOD FOR THE TREATMENT OF HYPEROPIA AND MYOPIA

This application claims the benefit of Provisional Application Serial No. 60/059,705, filed Sep. 22, 1997, which is hereby incorporated by reference herein in its entirety.

BACKGROUND OF THE INVENTION

1. Field of the Invention

This invention relates broadly to a medical device used in refractive surgery treatment to alter the curvature of the cornea. More specifically, this invention relates to a heating device which provides particular advantage in the treatment of hyperopia and astigmatism.

2. State of the Art

Refractive surgery is used to alter the curvature of the cornea to correct vision. Many techniques are currently employed to alter corneal curvature.

With respect to myopia, or "near-sightedness", the treatments of the art primarily aim to "flatten" the cornea; i.e., increase the radius of curvature of the cornea. For example, in radial keratotomy, a knife is used to make near full thickness incisions into the cornea to increase the radius of corneal curvature. The currently preferred tool of choice in the treatment of myopia is the excimer laser, which is used to selectively ablate corneal tissue and alter the corneal shape. In addition, other techniques using radio frequency waves or a holmium laser have also been used, whereby the corneal stroma is heated to induce an increased curvature of the cornea.

However, a convenient, effective, and safe method for treating hyperopia, or "far-sightedness", in which it is desired to decrease the corneal radius of curvature, has remained elusive. Refractive surgery for hyperopia has centered on the principal of inducing shrinkage of corneal tissues to "steepen" the central cornea. For instance, the holmium laser is used to heat the corneal stroma at several points around the visual axis. Upon heating, the stromal collagen (that is, the supporting tissue of the cornea) at these locations is induced to shrink and thereby reduce the radius of curvature of the central cornea. A similar approach has been advocated with the use of radio frequency waves, whereby electrodes are inserted into the corneal stroma and heated via current transmission or direct radio frequency waves to heat surrounding corneal tissues. As with the holmium laser techniques, the effect is to shrink collagen around the visual axis, and induce a steepening of the central cornea.

One of the main problems with these techniques is regression. After heating, the stromal collagen regresses toward its original conformation and shape and the hyperopia returns. Another problem is that uneven stromal collagen shrinkage at the heating points around the visual axis may result in irregular astigmatism, thereby exacerbating the visual deficiency.

Moreover, the excimer laser has not proved completely successful in treating hyperopia, primarily due to resulting stromal haze and regression.

SUMMARY OF THE INVENTION

It is therefore an object of the invention to provide a device which reliably, safely, and economically treats hyperopia.

It is another object of the invention to provide a device which reduces the radius of curvature of the cornea.

It is a further object of the invention to provide a device which substantially prevents uneven stromal collagen regression.

In accord with these objects, which will be discussed in detail below, a hyperopia correction system is provided which includes a device having an electrically-resistive ring, an insulative shaft coupled to the ring, and an electrical lead coupled to the ring, and an insulative handle coupled to the ring which facilitates manipulating the ring for placement on and removal from the cornea of the eye and through which the lead extends. The lead is couplable to a current source. According to a preferred aspect of the invention, a function generator is provided between the current source and the ring to generate a function of heat energy provided to the ring. The function generator permits very precise applications of current to the ring, and may be configured to heat the ring to a desired temperature, to maintain the temperature for a predetermined amount of the time, or to provide a heat profile (e.g., increasing and decreasing the temperature over a period of time). In addition, rings having particular diameters and widths may be selected to further control the size of the area which is heated.

Additionally, an astigmatism correction device, preferably operable in conjunction with the hyperopia heating device, is also provided. The device includes an element which is shaped to provide heat energy at two location 180° apart, and preferably fits within the annular opening of the hyperopia correction device. The device may be actively heated by the same power source as the hyperopia correction device, may be passively heated by the hyperopia correction device, or may be separately heated.

Alternatively, a combined hyperopia-astigmatism device is provided which includes generally elliptically-shaped ring which defines a long axis and short axis.

In use, the amount of hyperopia, and, where required, also the amount of astigmatism, to be corrected for a particular patient is determined. Anaesthetic is applied to the eye and a lamellar flap is produced to expose the corneal stroma bed. The annular heating element is placed on the stromal bed centered around the patient's fixation axis. If indicated, the astigmatism correction device is aligned with the pre-determined astigmatic axis of the flattest meridian of the cornea. If using the elliptically-shaped ring, the short axis is aligned with the flatter meridian of corneal astigmatism.

Once the device (or devices) are placed satisfactorily, the heating elements are heated, preferably in the range of 55 to 90 degrees Celsius. The controlled heating causes uniform and planar heating which shrinks the corneal collagen and thereby steepens the central corneal bed. The heating devices are then removed and the lamellar flap is re-positioned.

With the above embodiments, several advantages are provided. First, even heating of the corneal stroma is provided which provides greater and more stable corneal steepening. Second, the devices provide for careful alignment of the heating elements prior to treatment. Third, astigmatism can be treated. Fourth, the treatment is reproducible, particularly given the parametric control provided by the function generator.

Additional objects and advantages of the invention will become apparent to those skilled in the art upon reference to the detailed description taken in conjunction with the provided figures.

BRIEF DESCRIPTION OF THE DRAWINGS

FIG. 7 is a top view of refractive surgery utilizing a heating device according the invention adapted to treat hyperopia and astigmatism;

FIG. 8 is a bottom view of a third embodiment of a heating device according to the invention adapted to treat hyperopia and astigmatism;

FIG. 9 is a broken perspective view of a fourth embodiment of a heating device according to the invention adapted to treat hyperopia and astigmatism;

DETAILED DESCRIPTION OF THE PREFERRED EMBODIMENTS

Figure 1:
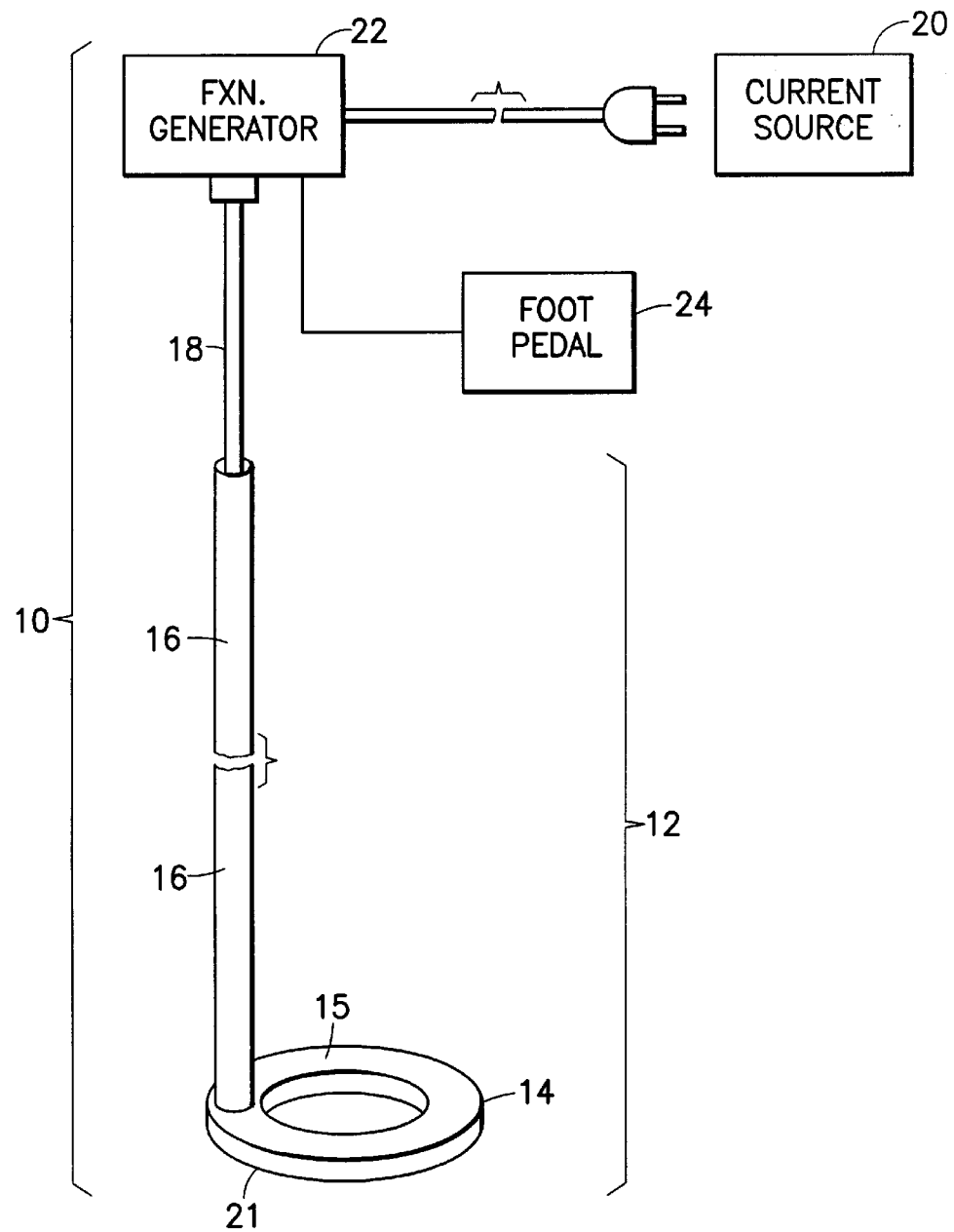
FIG. 1 illustrates a refractive surgery system according to the invention which includes a first embodiment of a heating device according to the invention.
Figure 2:
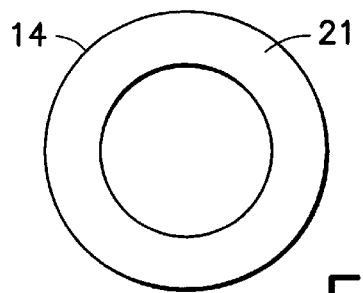
FIG. 2 is a bottom view of the heating device of FIG. 1 according to the invention.

Referring now to FIG. 1, a refractive surgery system 10 for performing corrective surgery on a hyperopic cornea is shown. According to the invention, the system 10 includes a heating device 12 comprising a preferably annular ring 14, a shaft 16 coupled to an upper surface 15 of the ring 14, and an electrically conductive lead 18 coupled to the ring 14 and preferably extending through shaft 16. The lead 18 is electrically couplable to a current source 20. The ring 14 is preferably made of an electrically resistive material, which when a current of known amplitude is passed through from the current source 20, the ring heats to a given temperature appropriate for shrinking corneal tissues, as described in more detail below. Referring to FIGS. 1 and 2, the ring 14 preferably includes a substantially planar and uniform lower surface 21.

Turning back to FIG. 1, the system 10 may include a plurality of heating devices 12, each having a ring with a particular diameter, width, and material composition, in order that the most appropriate ring with the required surface area, surface configuration, surface texture, and electrical resistance (i.e., to cause the ring to be heated to a particular temperature, given a particular current profile) may be used in the refractive surgical procedure, as described below. By way of example, and not by way of any limitation, the ring may have an outer diameter of approximately 7 mm, an inner diameter of approximately 6 mm, and a ring width of approximately 0.5 mm. The shaft is insulated and preferably made from a plastic or is rubber or Teflon® coated, thereby adapted to be manipulated by the hand of a physician while a current flows through the lead 18.

According to a preferred aspect of the invention, a function generator 22 is provided between the lead 18 and the current source 20. The function generator 22 permits very precise applications of current to the ring 14, and may be configured to heat the ring to a desired temperature, to maintain the temperature for a predetermined amount of the time, or to provide a heat profile (e.g., increasing and decreasing the temperature over a period of time). Preferably, the function generator 22 is activated by a foot pedal 24 to provide the selected function of current to the ring 14. Alternatively, other function generator activation means may be used. For example, the function generator may be manually activated.

Figure 3:
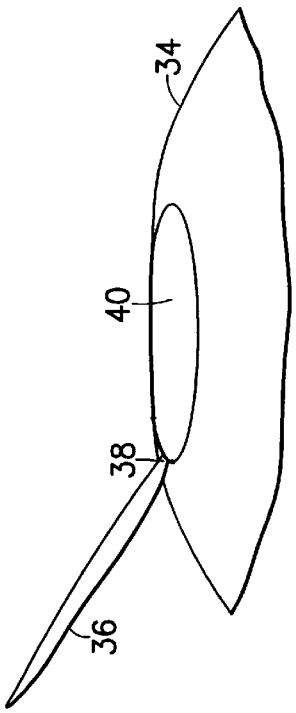
FIGS. 3 through 5 illustrate hyperopia refractive surgery using the heating device of FIG. 1 according to the invention.
Figure 4:
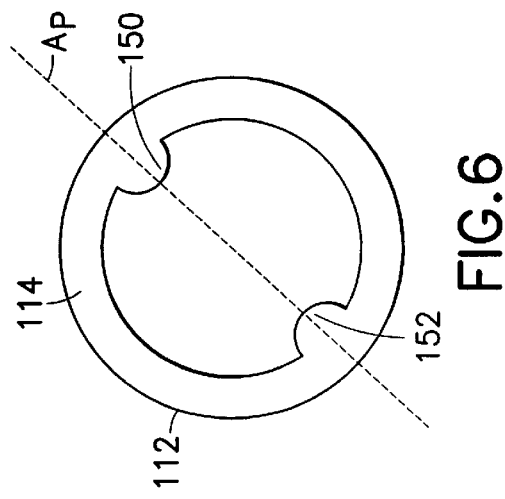
Figure 5:
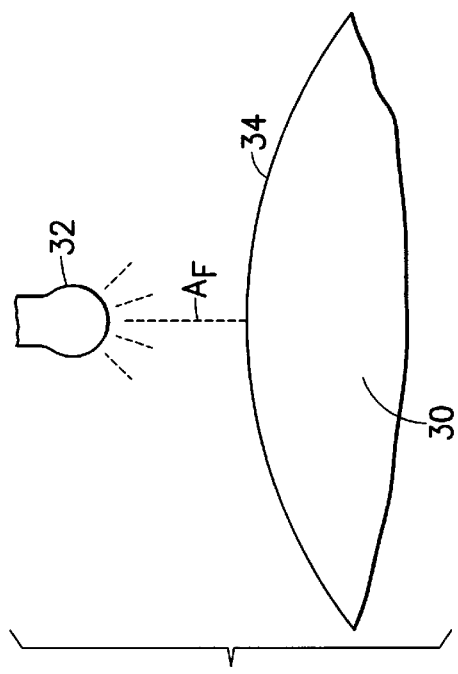

Turning now to FIG. 3, in use, the amount of hyperopia to be corrected is determined for the eye 30 of a given patient. The patient is placed in a supine position staring along an axis of fixation $A_F$ at a fixation light 32 directly in front of the eye 30. Topical anaesthetic is applied to the cornea 34 of the eye 30. Referring to FIG. 4, after the eye has been anaesthetized, a lamellar flap 36 is produced in a manner well known in the art, such as with the Chiron Corneal Shaper System™. Typically, the lamellar flap 36 is approximately 160 microns thick. The flap 36 is pulled back over a hinge region 38 to expose the corneal stromal bed 40. Turning now to FIG. 5, the patient is asked to stare at the fixation light 32 (FIG. 1) and the lower surface 21 of the ring 14 is placed against the stromal bed, with attention to positioning the center of the ring around the axis $A_F$ of the patient's fixation. The system 10 is then activated, for example via foot pedal 24, to cause a single pulse of current, or another function of current, to controllably and predictably heat the ring 14 to the desired temperature for a desired temporal profile. The heated ring 14 heats the stromal bed contacted by the bottom surface 21 of the ring. Annular heating of the stromal bed 40 results in shrinkage of the stromal collagen which decreases the radius of curvature of the cornea, correcting the hyperopia. The ring 14 is then removed from the stromal bed, and the lamellar flap 36 is repositioned over the altered stromal bed 40.

The instrument 10 and method described above provide several significant advantages. First, a relatively large ring-shaped region of the stroma is evenly heated (as opposed to heating a few points, as taught by the prior art), thereby providing greater and more stable corneal "steepening"; i.e., the reduction of the radius of curvature of the cornea. Second, the system enables relatively low temperature steepening, which results in less regression. Third, the system does not induce inflammation of the cornea, which, it is believed also reduces regression. Fourth, the system permits careful alignment of the ring prior to treatment. Fifth, the treatment is reproducible, particularly given the parametric control provided by the function generator.

Figure 6:
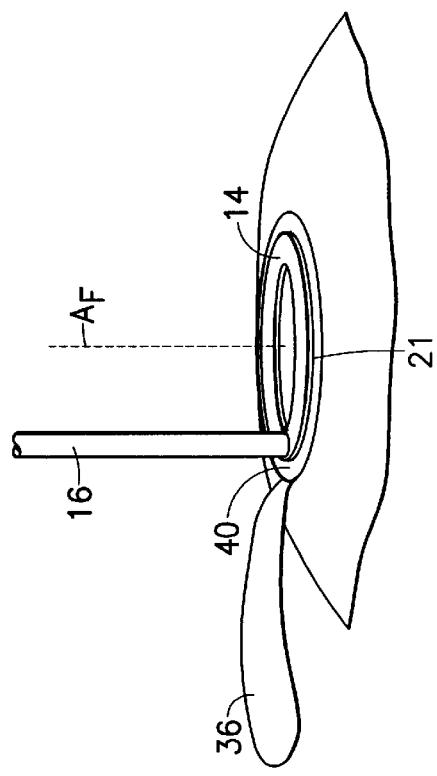
FIG. 6 is a bottom view of a second embodiment of a heating device according to the invention adapted to treat hyperopia and astigmatism.

Turning now to FIG. 6, a second embodiment of a heating device 112 according to the invention includes a ring 114 particularly suited for treating both hyperopia and astigmatism. The ring 114 is substantially circular and includes two preferably centrally-directed diametrically-opposed projections 150, 152 defining an axis $A_P$.

Referring to FIG. 7, prior to surgery for hyperopia and astigmatism, the direction of astigmatic correction for the cornea 134 is determined, in addition to the desired hyperopic correction. By manipulating the shaft 116, the axis $A_P$ of the ring 114 is aligned on the stromal bed over the astigmatic axis $A_A$ of the flattest meridian. After the ring 114 is satisfactorily aligned, the ring is heated to shrink the stromal collagen thereunder and correct the visual deficiency. The ring 114 is then removed from the stromal bed, and the lamellar flap 136 is repositioned over the altered stromal bed 140.

It will be appreciated that rings of other shapes and constructs maybe used to correct both the hyperopia and astigmatism in a single procedure. Turning now to FIG. 8, a third embodiment of a heating device 212 according to the invention includes a ring 214 which is substantially elliptical in shape. The shape defines a long axis $A_L$ and a short axis $A_S$. In use, the short axis $A_S$ is aligned with the astigmatic axis of the flattest meridian.

Figure 11:
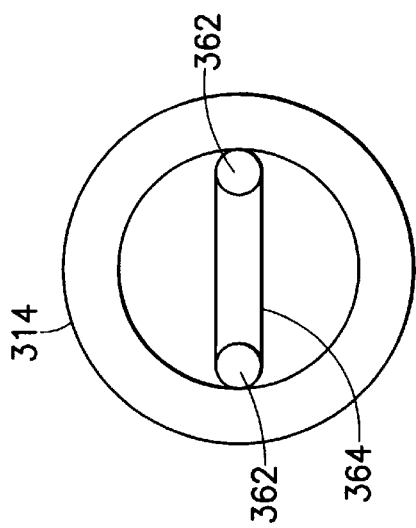
FIG. 11 is a bottom view of the heat device shown in FIG. 9.
Figure 10:
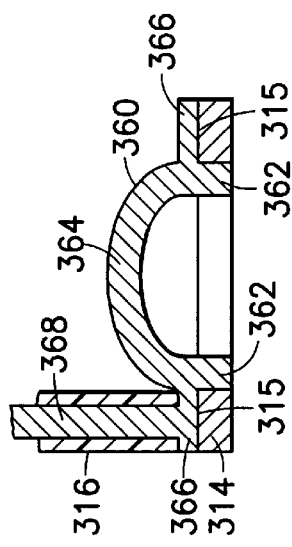
FIG. 10 is a section view through line 10—10 in FIG. 9.

Referring now to FIGS. 9 through 11, a fourth embodiment of a heating device 312 according to the invention includes a substantially annular ring 314 coupled to a shaft 316 and lead 318, as described above with respect to the first embodiment. The device 312 further includes a distinct astigmatism correction heating element 360, which may be of the same material or a different material from the ring 314. The heating element 360 includes two spot heating locations 362, a bridge portion 364 which bridges the spot heating locations 362, and two lip portions 366 which rest on the upper surface 315 of the annular ring 314. The heating element 360 also includes a shaft 368 and a lead 370 permitting independent manipulation and heating thereof; i.e., the heating element 360, as a result of the material of construction and the amplitude and time of current passed through, may be heated to a different temperature than the ring 314. The bridge portion 364 may be provided off-axis to provide the physician with an unobstructed view through the center of the ring 314.

Figure 13:
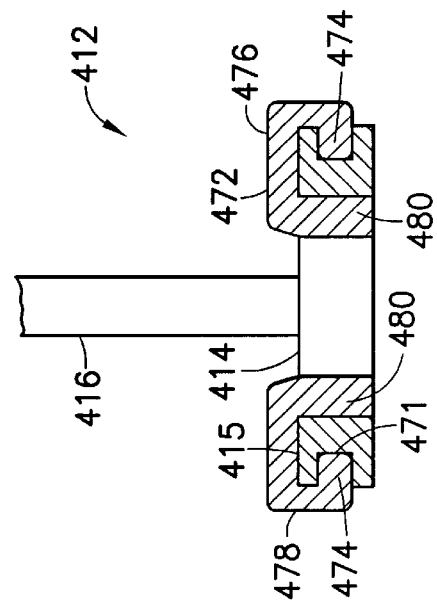
FIG. 13 is a section view across line 13—13 in FIG. 12
Figure 12:
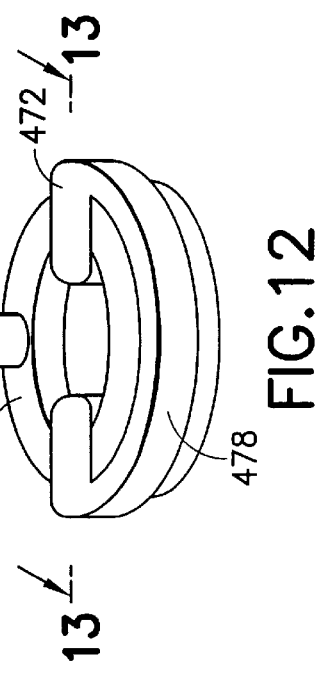
FIG. 12 is a broken perspective view of a fifth embodiment of a heating device according to the invention adapted to treat hyperopia and astigmatism.

Turning now to FIGS. 12 and 13, a fifth embodiment of a heating device 412 according to the invention includes a shaft 416 having at the distal end thereof a substantially annular ring 414 provided with a peripheral circumferential track 471. A second heating element 472 is also provided and includes a peripheral inwardly projecting portion 474, an upper lip portion 476, a side wall 478, and two descending spot heating locations 480. The second heat element is curved preferably approximately 180° about a radius. The annular and second heating elements 414, are coupled together such that the second heating element may rotate about the track 471 of the annular heating element. In this manner the physician may optimally orient the spot locations 480 relative to the shaft 416 in order to facilitate the corrective procedure.

There have been described and illustrated herein several embodiments of a system, and components thereof, for the correction of the hyperopia and astigmatism. While particular embodiments of the invention have been described, it is not intended that the invention be limited thereto, as it is intended that the invention be as broad in scope as the art will allow and that the specification be read likewise. Thus, while particular materials for the shaft, and heating elements have been disclosed, it will be appreciated that other materials which provide the desired results may be used. Furthermore, while a function generator is described for use with the system, it will be appreciated that the function generator is not necessary, but rather only desirable. Also, while particular shapes have been disclosed for the heating rings, it will be appreciated that other shapes may likewise be used. Moreover, while particular "spot" heating elements for the treatment of astigmatism have been disclosed, it will be appreciated that other configurations could be used as well. Also, while particular exemplar dimensions for the ring have been disclosed, it will be understood that other dimensions may be used. In addition, while particular embodiments of the heating device have been shown with diametric protuberances on the inside of the heating ring, it will be appreciated that, while not preferred, such protuberances may be provided at the outer periphery of the heating ring. Furthermore, a substantially circular ring may be provided with a first lead for generally heating the ring to a first desired temperature and one or more additional leads for selectively heating diametrically opposed portions of the ring to a higher temperature, and thereby enable astigmatic correction with a single circular ring. Moreover, while the ring preferably has a planar lower surface, it will be appreciated that the ring may be toroidal in shape. Furthermore, greater or lesser effect can be achieved in any of the previously described heating elements by controlling the texture of the surface of the heating element positioned against the stromal bed, by controlling the width and thickness of the heating element and material composition of the heating element, and by varying the degree and duration of heating. It will therefore be appreciated by those skilled in the art that yet other modifications could be made to the provided invention without deviating from its spirit and scope as so claimed.

What is claimed is:

1. A system for reducing the radius of curvature of a cornea, the cornea having collagen tissue, said system for use with a current source and comprising:

a) an electrically resistive ring element having a substantially planar heating surface;

b) an insulative handle coupled to said ring element;

c) an electrically conductive lead having a first end electrically coupled to said ring element and a second end; and d) an activatable generation means for generating a current profile from the current source, said second end of said lead being coupled to said generation means, wherein when said generation means is activated, said current profile causes said heating surface of said ring element to controllably heat to a temperature sufficient to cause the collagen tissue to shrink but not to be seared.

2. A system according to claim 1, wherein:

said temperature sufficient to cause the collagen tissue to shrink is approximately between 55 and 90 degrees Celsius.

3. A system according to claim 1, wherein:

said handle is tubular and said lead extends through said handle.

4. A system according to claim 1, wherein:

said handle includes a conductive inner member and an outer insulative coating.

5. A system according to claim 1, further comprising:

e) a foot pedal which activates said generation means.

6. A system according to claim 1, wherein:

said ring element is substantially circular shaped.

7. A system according to claim 1, wherein:

said ring element is substantially elliptically shaped.

8. A system according to claim 1, further comprising:

e) a current source to which said generating means is couplable.

9. A system for reducing the radius of curvature of a cornea, the cornea having collagen tissue, said system for use with a current source and comprising:

a) an electrically resistive ring element wherein said ring element is substantially circular, defines a diameter, a circumference, and includes two diametrically-opposed protuberances about said circumferences;

b) an insulative handle coupled to said ring element;

c) an electrically conductive lead having a first end electrically coupled to said ring element and a second end; and d) an activatable generation means for generating a current profile from the current source, said second end of said lead being coupled to said generation means, wherein when said generation means is activated, said current profile causes said ring element to heat to a temperature sufficient to cause the collagen tissue to shrink.

10. A system according to claim 8, wherein:

said circumference is an inner circumference.

11. A system according to claim 6, further comprising:

e) a heating element having first and second spot heating portions and means for stabilizing said heating element with said ring element such that said first and second heating portions are substantially aligned on said diameter.

12. A system according to claim 11, wherein:

said ring element and said heating element are comprised of different materials.

13. A system according to claim 11, further comprising:

f) a second handle coupled to said heating element; and g) a second lead having a first end coupled to said heating element and a second end electrically couplable to the current source.

14. A system according to claim 13, wherein:

said ring element and said heating element are independently heatable.

15. A system according to claim 11, wherein:

said heating element is coupled to and rotatable relative to said ring element.

16. A heating device for use with a current source for reducing the radius of curvature of a cornea, said heating device comprising:

a) a ring-shaped first heating element;

b) an insulative handle coupled to said first heating element;

c) an electrically conductive lead having a first end electrically coupled to said ring element and a second end couplable to the current source; and d) a second heating element having first and second spot heating portions and means for stabilizing said second heating element with said first heating element.

17. A heating device according to claim 16, wherein:

said ring shaped heating element is circular in shape and defines a diameter, and said means for stabilizing said second heating element substantially align said first and second heating portions on said diameter.

18. A heating device according to claim 16, wherein:

said second heating element is rotatable relative to said first heating element.

19. A heating device according to claim 16, further comprising:

e) a second handle coupled to said second heating element; and f) a second lead having a first end coupled to said second heating element and a second end couplable to the current source.

20. A heating device for use with a current source for reducing the radius of curvature of a cornea, said heating device comprising:

a) an annular ring-shaped heating element defining a diameter, an inner circumference, and including two diametrically-opposed protuberances about said inner circumference;

b) an insulative handle coupled to said ring-shaped heating element; and c) an electrically conductive lead having a first end electrically coupled to said ring-shaped element and a second end couplable to the current source.

21. A heating device according to claim 20, wherein:

said heating element includes a planar lower surface which is adapted to be positioned against the cornea.

22. A method of reducing the radius of curvature of the cornea of the eye, comprising:

a) creating a lamellar flap in the cornea to expose the corneal stroma;

b) positioning a ring-shaped heating element on the corneal stroma;

c) heating the heating element to cause shrinkage of collagen in the stroma such that the radius of curvature of the cornea is decreased; and d) repositioning the lamellar flap over the corneal stroma.

23. A method according to claim 22, wherein:

said ring-shaped heating element is circular and provided with two diametrically-opposed protuberances about a circumference of said element, and said positioning further comprises aligning the protuberances on the flattest meridian of astigmatism.

* * * * *